(12) United States Patent
Long et al.

(10) Patent No.: US 11,304,672 B2
(45) Date of Patent: Apr. 19, 2022

(54) IMAGING SYSTEM HOUSING

(71) Applicant: CapeRay Medical (Pty) Ltd, Westlake Business Park (ZA)

(72) Inventors: James William Long, Kirstenhof (ZA); Raphael V. Smith, Observatory (ZA); Christopher Leonard Vaughan, Newlands (ZA); Roland Victor Baasch, Cape Town (ZA)

(73) Assignee: CapeRay Medical (Pty) Ltd, Westlake Business Park (ZA)

( * ) Notice: Subject to any disclaimer, the term of this patent is extended or adjusted under 35 U.S.C. 154(b) by 62 days.

(21) Appl. No.: 16/875,541

(22) Filed: May 15, 2020

(65) Prior Publication Data
US 2020/0405251 A1 Dec. 31, 2020

Related U.S. Application Data

(60) Provisional application No. 62/868,263, filed on Jun. 28, 2019.

(51) Int. Cl.
*A61B 6/02* (2006.01)
*A61B 8/08* (2006.01)
*A61B 6/00* (2006.01)

(52) U.S. Cl.
CPC .............. *A61B 6/502* (2013.01); *A61B 6/025* (2013.01); *A61B 6/4283* (2013.01); *A61B 6/5247* (2013.01); *A61B 8/0825* (2013.01); *A61B 8/5261* (2013.01)

(58) Field of Classification Search
None
See application file for complete search history.

(56) References Cited

U.S. PATENT DOCUMENTS

| 9,636,073 B2 | 5/2017 | Evans et al. |
| 10,220,574 B2 | 3/2019 | Smith |
| 2004/0202279 A1* | 10/2004 | Besson ............... A61B 6/544 378/37 |
| 2013/0281840 A1 | 10/2013 | Vaughan et al. |
| 2017/0227031 A1* | 8/2017 | Boo ..................... F16B 12/46 |

FOREIGN PATENT DOCUMENTS

WO  WO-2016075648 A1 *  5/2016  ............. A61B 6/502

* cited by examiner

*Primary Examiner* — Colin T. Sakamoto
(74) *Attorney, Agent, or Firm* — Christopher M. Scherer; DeWitt LLP

(57) ABSTRACT

An imaging system housing is provided which includes a body and a scanning plate. The body defines a cavity and an opening in communication with the cavity. The body includes one of a lip or groove formation extending from peripheral zone adjacent the opening in a direction away from or towards the cavity and transverse to a plane defined by the opening. The scanning plate is shaped and dimensioned to close the opening and has the other of a groove or lip formation extending along a periphery thereof and being shaped and dimensioned to cooperate with and receive the lip or groove formation of the body. The scanning plate is made from a low surface energy plastic material. The body and plate are bonded together using a structural acrylic adhesive applied to one or both of the lip and groove formations. The imaging system may be a dual-modality imaging system.

14 Claims, 12 Drawing Sheets

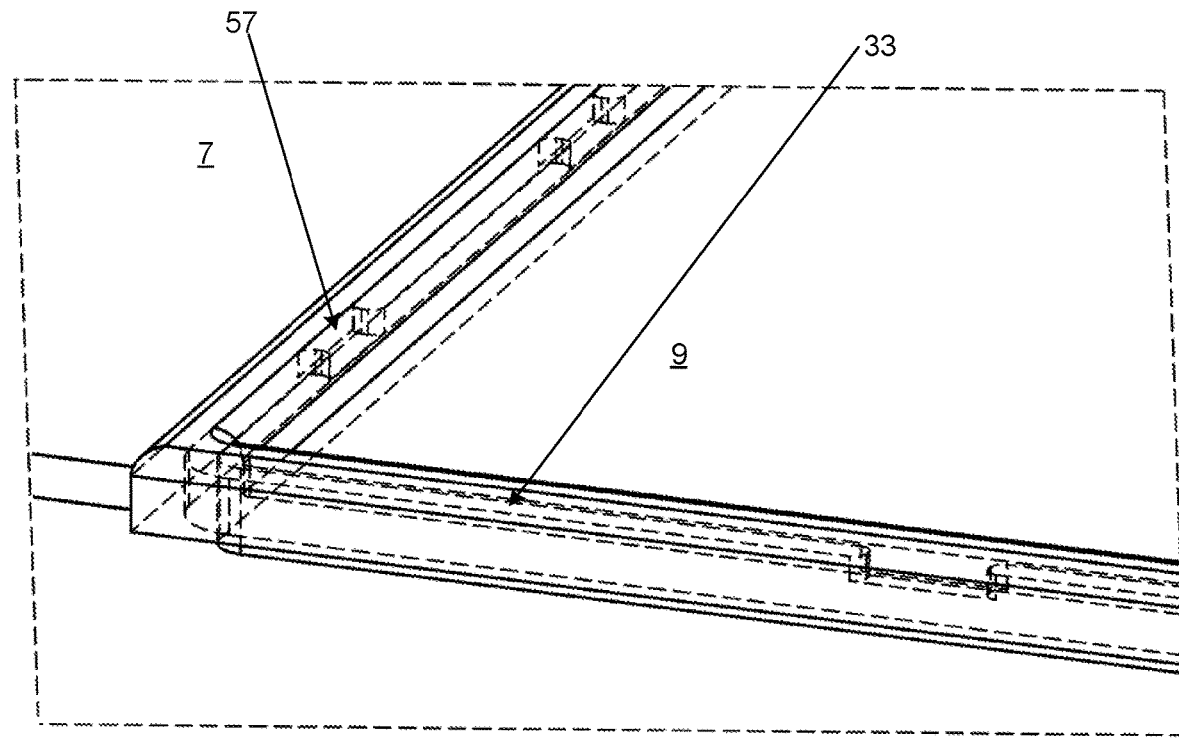
Figure 13
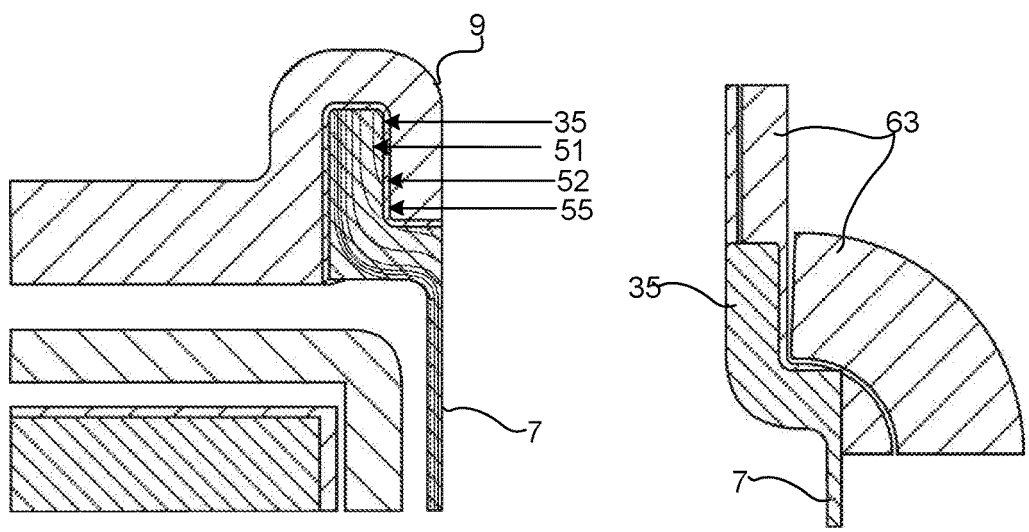
Figure 14
Figure 15

IMAGING SYSTEM HOUSING

CROSS-REFERENCE TO RELATED APPLICATIONS

This application claims priority from U.S. provisional patent application No. 62/868,263 filed on 28 Jun. 2019, which is incorporated by reference herein.

FIELD OF THE INVENTION

The invention relates to an imaging system housing and method of manufacturing an imaging system housing. The invention may find particular but not exclusive application in housing components of a dual-modality imaging system, such as an X-ray detector and ultrasonic transducer.

BACKGROUND TO THE INVENTION

Dual-modality imaging systems that use a combination of full-field digital mammography and automated breast ultrasound imaging in a single device are known. These devices combine the benefits of both imaging techniques to obtain more effective and accurate diagnosis of carcinoma or other abnormalities in particularly breast tissue.

For example, such dual-modality scanning apparatuses that incorporate both X-ray and ultrasound technologies are disclosed in US2013/281840 and U.S. Pat. No. 9,636,073. In use of such apparatuses, biological tissue to be scanned, typically a breast, is compressed between a first surface, also referred to as a scanning plate or compression plate, and a compression paddle which is mechanically lowered onto the biological tissue. The scanning plate can form part of a housing within which a dual modality scanning element comprising an X-ray detector and ultrasonic transducer are mounted on a drive below the scanning plate. Such a dual modality scanning element enables simultaneous acquisition of X-ray and ultrasound images of the biological tissue compressed between the scanning plate and the compression paddle. The scanning element moves on the drive in a plane parallel to the scanning plate for imaging of the tissue through the scanning plate and parallel to a plane defined by the transverse movement of the X-ray source. A linear drive means is provided that moves the scanning element along rails.

The housing is typically required to be hermetically sealed and filled with a non-conductive fluid with an acoustic impedance resembling that of the tissue, completely immersing the scanning assembly and drive in the fluid. The fluid may provide ultrasonic coupling between the scanning assembly and the tissue in use. A hermetic seal maintains the fluid at a constant volume during use. Due to the sealed and filled nature of the housing, the housing is substantially less compressible than it would have been had it not been for the presence of the fluid. The incompressibility of the housing allows both the X-ray detector and ultrasound transducer to move and scan very close to the underside of the scanning plate (and hence the biological tissue), which minimizes X-ray signal attenuation that may be caused by the fluid and the geometric magnification due to the finite X-ray focal spot. Prior to filling the housing, the fluid may be de-gassed, for example using a vacuum with agitation.

The hermetically sealed housing must be devoid of water and air to minimize interference with the acoustic impedance of the fluid. During manufacturing of the scanning assembly, the filled housing is drained and dried to remove all water and air.

The scanning plate of the housing may be made from polymethylpentene, a thermoplastic material better known commercially by its trade name "TPX" (a trademark of MITSUI CHEMICALS) and referred to herein as "PMP". PMP is a lightweight polyolefin with exceptional acoustical and electrical properties. PMP has low moisture absorption and excellent chemical resistance. It is often used for applications requiring low distortion of sound waves including sonar covers, speaker cones, and ultrasonic transducer heads.

Efforts to secure a PMP plate which forms the scanning plate to a body of a housing include the use of a stitched bond or an adhesive bond. Stitched bonding requires the use of stitching, together with an O-ring and a suitable sealant (e.g. Vitaflex). Using an adhesive bond entails use of an adhesive to bond the PMP plate to the housing. After bonding, more ductile epoxy is used to waterproof the bond. However, PMP has an unusually low surface tension (24 mN/m) and the epoxy does not adhere to it adequately. In fact, PMP exhibits excellent peel ability and is often used as a release material at the time of curing thermosetting resins or the like. For this reason, the application of epoxy to the PMP scanning plate is a cumbersome step in the manufacturing of a hermetically sealed housing incorporating a PMP scanning plate and may not provide an adequate seal.

The body of the housing, which may have an edge of less than 1 mm thick, needs to be made from a suitably stiff material capable of supporting a compression load of approximately 200 N. The housing is therefore preferably, but not exclusively, made from carbon fiber-reinforced polymers (CFRP). Such materials are easily moldable into the required shape. To manufacture the entire housing from PMP is not feasible as the material is not stiff enough.

U.S. Pat. No. 10,220,574 aims to address the above described deficiencies by providing a method of assembling a composite housing for a scanning assembly in which a body of the housing defines an opening of a first perimeter and a polymethylpentene scanning plate is provided which has a lip with a marginally larger perimeter than the first perimeter. During assembly of the composite housing, at least a part of scanning plate is thermally contracted to allow it to be positioned within the opening such that the peripheral side surface of the scanning plate faces the edge of the body. When the scanning plate returns to ambient temperature and expands at least a portion of the side surface of the scanning plate engages the edge of the body.

While this method may be effective, it can be difficult to implement in practice. This may be due to non-uniform contraction of the PMP, which can lead to leaks, and due to the different thermal expansion coefficients of PMP and CFRP, which, during operation of the system, can result in the PMP plate moving relative to the CFRP housing and cause leaks. There is accordingly a need for a method of securing PMP to a body, preferably made of CFRP, in a way that provides adequate sealing characteristics.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with an aspect of the invention there is provided an imaging system housing comprising a body and a scanning plate, the body defining a cavity and an opening in communication with the cavity, the body including one of a lip or groove formation extending from peripheral zone adjacent the opening in a direction away from or towards the cavity and transverse to a plane defined by the opening, the scanning plate being shaped and dimensioned to close the opening and having the other of a groove or lip formation extending along a periphery thereof and being shaped and dimensioned to cooperate with and receive the lip or groove formation of the body, wherein the scanning plate is made from a low surface energy (LSE) plastic material, and wherein the body and plate are bonded together using a structural acrylic adhesive applied to one or both of the lip and groove formations.

The scanning plate may be made from polymethylpentene.

The groove and lip formations may include cooperating castellations at locations along the lengths thereof; and, the width to height ratio of the lip formation may be in the range of 1:1.00 to 1:4.00.

The body may be made from a fiber-reinforced polymer and may include the lip formation, wherein the scanning plate includes the groove formation, and wherein the lip formation extends away from the cavity and transverse to the plane defined by the opening; fibers of at least portions of the fiber-reinforced polymer which form at least part of the lip formation may extend transverse to a plane defined by the opening and may thus extend generally parallel to the direction in which the lip elements extend; the lip formation may include lip elements extending along each side of the opening and corner pieces which join the lip elements to define a lip which surrounds the opening; fibers of the fiber-reinforced polymer which form the lip elements extend transverse to a plane defined by the opening and may thus extend generally parallel to the direction in which the lip elements extend; the fiber-reinforced polymer may be a carbon fiber-reinforced polymer.

The housing may be hermetically sealed, wherein components of an imaging system locate within the cavity and wherein the housing is filled with a non-conductive fluid having a specific acoustic impedance. In some embodiments, the housing may be configured to house an X-ray detector and ultrasonic transducer below the scanning plate.

In other embodiments, the housing may include a formation configured to receive a flat panel detector of an imaging device, wherein the formation defines a recess which is shaped and dimensioned to receive the flat panel detector, and wherein the formation is defined at a location relative to the cavity of the body so as to orient operatively the scanning plate parallel to and directly above an operatively upper surface of the flat panel detector.

The groove formation may define a groove which surrounds the scanning plate. The opening and scanning plate may be generally rectangular in shape.

In accordance with an aspect of the invention there is provided a method of manufacturing an imaging system housing comprising molding fiber-reinforced polymer into the shape of a body of the housing, the body defining a cavity and an opening in communication with the cavity, the body including a lip formation extending from peripheral zone adjacent the opening in a direction away from the cavity and transverse to a plane defined by the opening, wherein molding the fiber-reinforced polymer includes controlling the direction of fibers of the fiber-reinforced polymer so that fibers which form at least a part of the lip formation extend generally parallel to the direction in which the lip formation extends.

The fiber-reinroced polymer may be molded with excess material which is manipulated to control the fiber direction; the excess material may be added as separate portions of carbon fiber-reinforced polymer material which become integrally formed to provide a unibody; the separate portions of material may be added with fibers thereof extending parallel to fibers already constituting the body and are arranged to facilitate correct fiber direction of the lip formation; the carbon fiber-reinforced polymer may be pre-impregnated and may be molded onto a shell which defines the shape of the body; the shell may be a male mold made up of two parts which are detachably secured to each other.

Embodiments of the invention will now be described, by way of example only, with reference to the accompanying drawings.

BRIEF DESCRIPTION OF THE DRAWINGS

In the drawings:

FIG. 13 is an enlarged three-dimensional view illustrating cooperation of the lip and groove formations and castellations thereof in which the scanning plate is illustrated as being transparent to illustrate components behind it;

FIG. 14 is a schematic diagram which illustrates fiber orientation of the carbon fiber-reinforced polymer from which a lip element of the lip formation of the body of the housing is formed;

FIG. 15 is a schematic diagram which illustrates, in a manufacturing process, that part of the pre-machined, molded body that is machined to define the body of the housing of FIG. 3;

DETAILED DESCRIPTION WITH REFERENCE TO THE DRAWINGS

Figure 1:
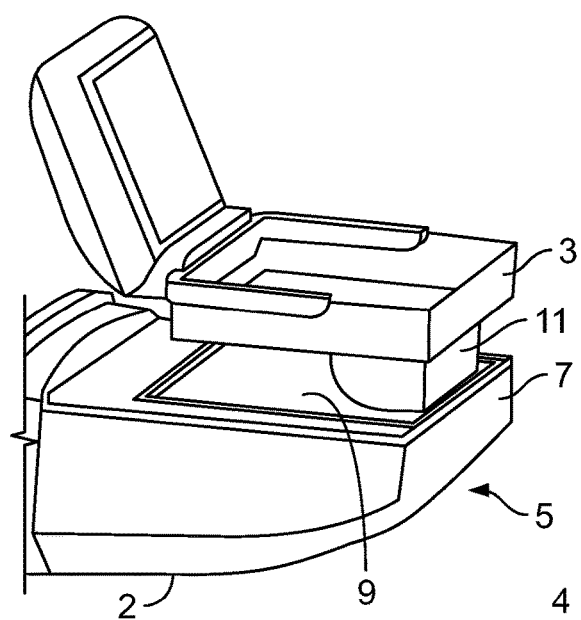
FIG. 1 is an enlarged three-dimensional view of components of a dual-modality scanning apparatus according to aspects of the present disclosure.
Figure 2:
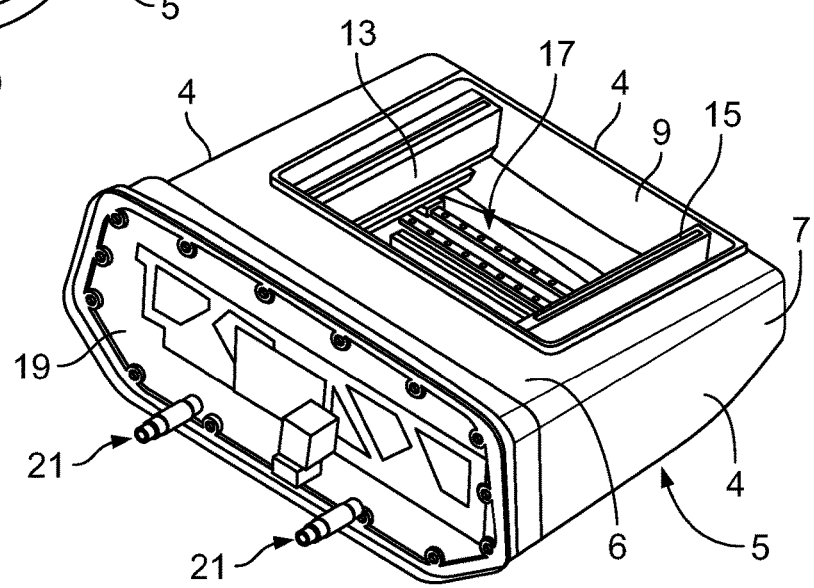
FIG. 2 is a three-dimensional view of a housing of a dual-modality scanning apparatus including a body and a scanning plate according to aspects of the present disclosure, in which Figure the scanning plate is illustrated as being transparent to illustrate components housed within the housing.
Figure 3:
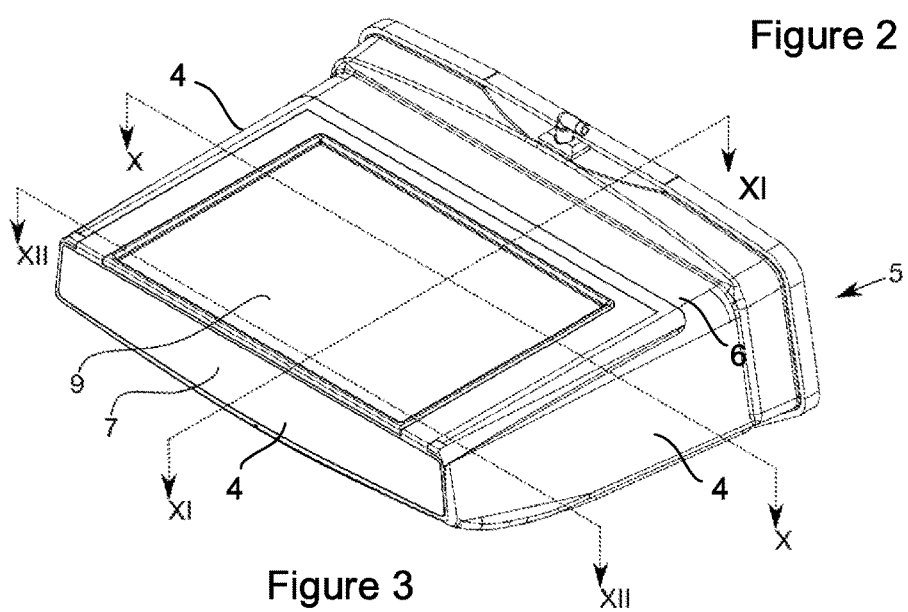
FIG. 3 is a three-dimensional view of a housing of a dual-modality scanning apparatus including a body and a scanning plate according to aspects of the present disclosure.
Figure 4:
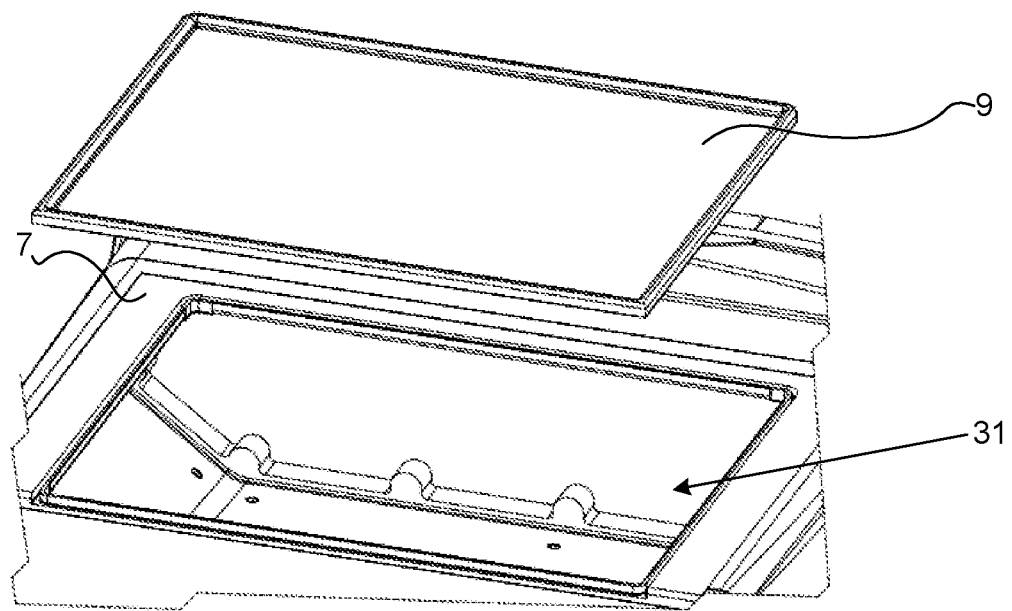
FIG. 4 is a three-dimensional view of the body and scanning plate of the housing of FIG. 3, with the scanning plate spaced apart from the opening in which it locates in use.
Figure 5:
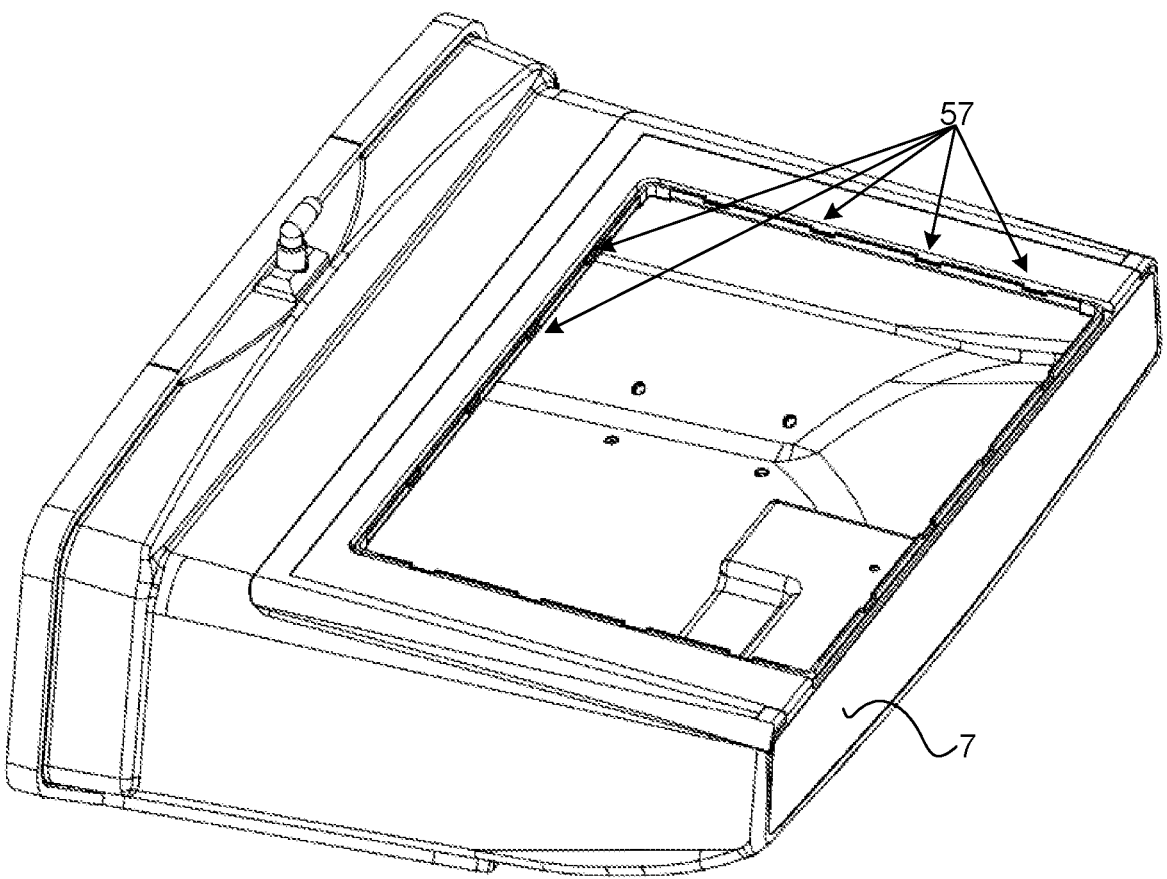
FIG. 5 is a three-dimensional view of the body of the housing of FIG. 3.
Figure 6:
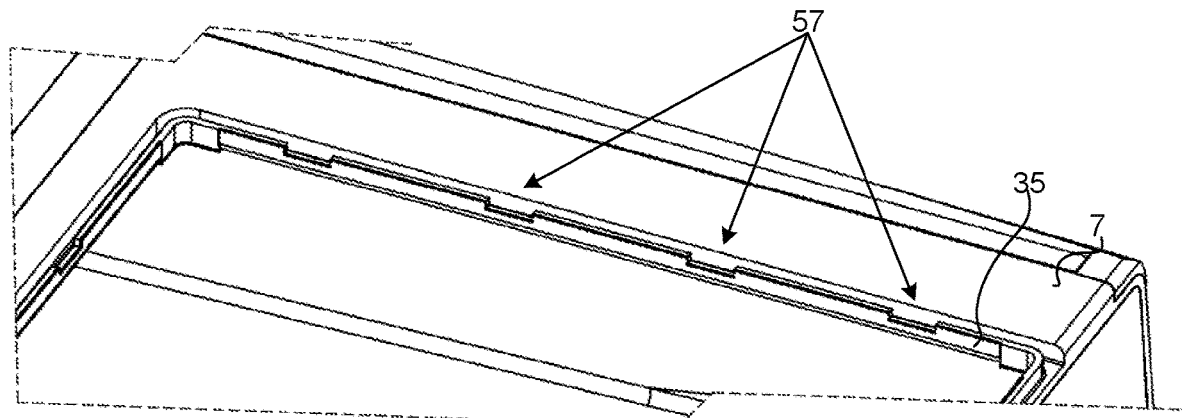
FIG. 6 is an enlarged three-dimensional view of the body of the housing of FIG. 3 showing more clearly the lip formation thereof.
Figure 7:
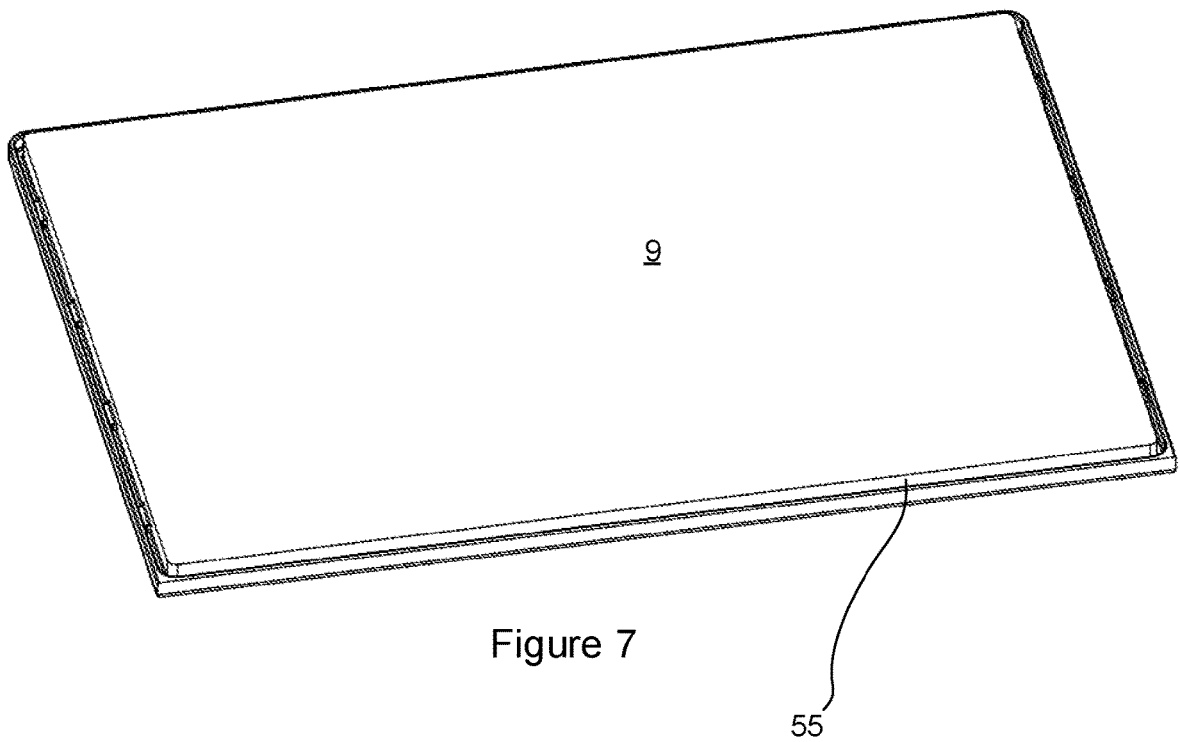
FIG. 7 is a three-dimensional view of an operatively underside of the scanning plate of FIG. 3.
Figure 8:
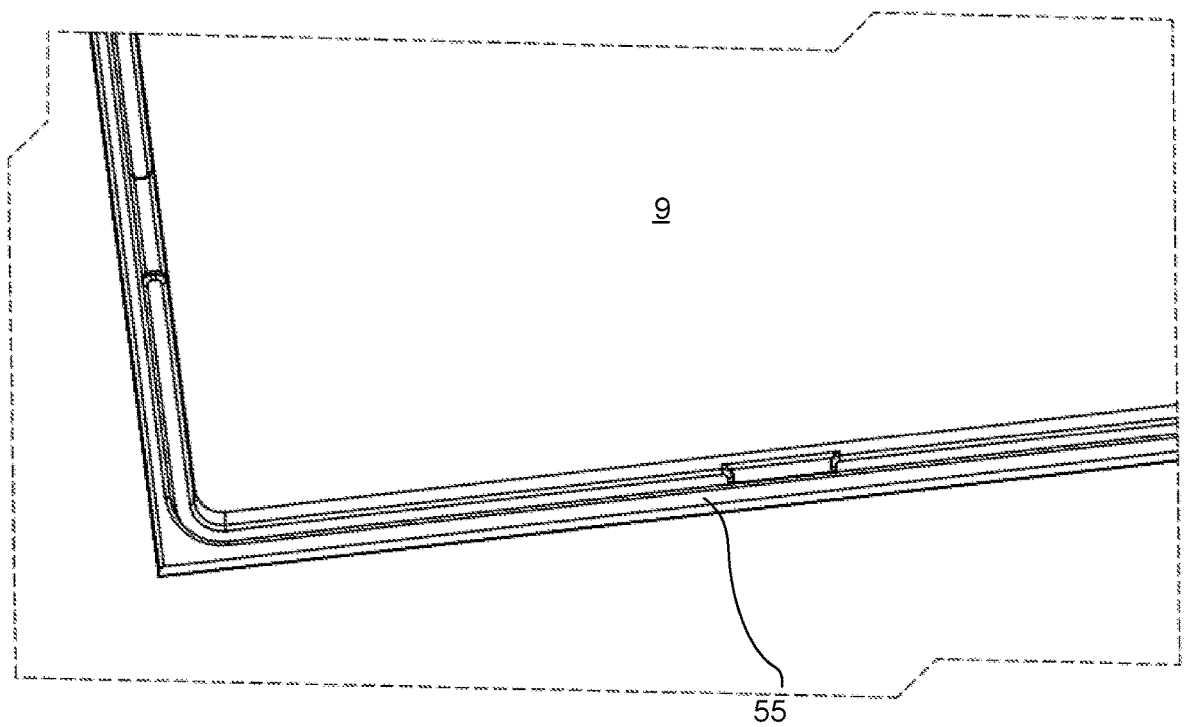
FIG. 8 is an enlarged three-dimensional view of the underside of the scanning plate of FIG. 3 showing more clearly the groove formation thereof.

Aspects of the present disclosure relate to imaging devices or apparatuses, and particularly to dual-modality scanning apparatuses which incorporate both X-ray and ultrasound technologies. Such dual-modality scanning apparatuses may combine full-field digital mammography and automated breast ultrasound imaging in a single device to obtain more effective and accurate screening for abnormalities in biological tissue. The dual-modality scanning apparatuses described herein may find particular application in screening for carcinoma or other abnormalities typically present in breast tissue, although other applications should not be excluded.

As will be explained below, in some embodiments, the dual-modality scanning apparatus may be provided as a standalone unit which includes both X-ray and ultrasound imaging technologies, while in other embodiments, the dual-modality scanning apparatus may be provided by way of after-market modification (or retrofit) of a mammography device that supports digital breast tomosynthesis (DBT). Such after-market modification may entail attaching or securing an ultrasound device to the mammography device so as to provide dual-modality scanning functionality to an operational device.

Aspects of the present disclosure relate particularly to the housing in which components of an imaging device may be housed. The imaging device may be a dual-modality scanning apparatus or an ultrasound imaging device which is provided to operate together with a mammography device in order to provide an after-market dual-modality scanning apparatus. The housing includes a body defining a cavity and an opening in communication with the cavity. The body may include a lip or wall formation extending generally from a peripheral zone adjacent the opening in a direction away from the cavity and transverse to a plane defined by the opening. The body may be made from a fiber-reinforced polymer, such as a carbon fiber-reinforced polymer or the like. The housing further includes a scanning plate shaped and dimensioned to close the opening and which may have a groove or slot formation extending along a periphery thereof and being shaped and dimensioned to cooperate with and receive the lip formation. The scanning plate may be made from a suitable plastics material, which may be a low surface energy (LSE) plastic material, such as polymethylpentene ("PMP").

The lip and groove formations may surround the opening and scanning plate, respectively. The body and plate may be bonded together using a suitable bonding agent, such as a structural acrylic adhesive, applied to one or both of the lip and groove formations. The housing may be hermetically sealed and may be filled with a non-conductive fluid with a suitably selected acoustic impedance (e.g. so as to resemble that of biological tissue), so as to immerse components housed therein in the fluid.

The lip and groove formations may be provided to maximize the bonded surface area and thus improve the strength of the bond. In some embodiments, the lip formation may have a width to height ratio in the range of 1:1.00 to 1:4.00, so as to maximize shear loading (which is loading in a direction parallel with that of the gap between major surfaces of the lip and groove formations) of the adhesive. Any suitable structural acrylic adhesive may be used, for example 3M™ Scotch-Weld™ Structural Plastic Adhesive DP8005, DP8010 or the like ("3M" and "Scotch-Weld" are trademarks of 3M COMPANY). It should however be appreciated that any suitable bonding agent that can bond low surface energy (LSE) plastics with minimal to no surface preparation may be used. For example, in some implementations an adhesive selected from the group of Loctite™ 3035 (LOCKTITE is a trademark of the HENKEL CORPORATION), Permabond™ TA4605 and TA4610 (Permabond is a trademark of PERMABOND LLC), Master Bond™ MB514 (Master Bond is a trademark of MASTER BOND INC.), Bond It™ B-45TH (Bond It is a trademark of SEAL IT SERVICES) or the like may be used.

In some implementations, fibers of the fiber-reinforced polymer (which may also be termed "the composite") from which at least portions (or elements) of the lip formation are formed may be aligned with an axis of the plane defined by the opening (or, in other words, transverse to the plane defined by the opening). This may, in operation, align the fibers with the direction of a force exerted on the scanning plate, and in turn the adhesive. Such a force may be caused by the sealed and filled nature of the housing. As will be explained in greater detail below, this aligns the fibers and adhesive such that they experience favorable loading during the expected use cases of the housing. Such a fiber direction may increase strength of the adhesive joint geometry.

FIG. 1 illustrates components of an example dual-modality scanning apparatus which includes a compression paddle (3) and a housing (5) having a body (7) providing a scanning plate (9). The compression paddle (3) may be configured for mechanical lowering onto and compression of biological tissue (11) supported on the scanning plate. Example embodiments of a housing and scanning plate according to aspects of the present disclosure are illustrated more clearly in FIGS. 2 to 14.

The housing (5) may house a dual modality scanning element comprising an X-ray detector (13) and ultrasonic transducer (15). One or both of the X-ray detector (13) and ultrasonic transducer (15) may be mounted on rails (17) below the scanning plate (9). Such a dual modality scanning element may enable simultaneous acquisition of X-ray and ultrasound images of the biological tissue (11) compressed between the scanning plate (9) and the compression paddle (3). The scanning element moves on the rails (17) in a plane parallel to the scanning plate (9) for imaging of the tissue (11) through the scanning plate (9) and parallel to a plane defined by the transverse movement of the X-ray source. A linear drive means is provided that moves the scanning element along the rails (17). A backplate (19) of the housing (5) provides hydraulic connectors (21), electrical connectors (not shown) and ultrasound cable glands (not shown) for interfacing components housed within the housing (5) with external components. The housing (5) may provide a hermetically sealed platform in which the dual modality scanning element may be located.

The body (7) of the housing (5) is made up of a bottom wall (2), a top wall (6) and side walls (4) which join the top wall (6) to the bottom wall (2). In the illustrated embodiment, three side walls (4) are provided, with an aperture being left open for closing by way of the backplate (19). The bottom wall (2) may be inclined relative to the top wall (6), with the side walls (4) being shaped and dimensioned appropriately such that the housing narrows from the aperture towards the opposing side wall. There may be one or more steps defined in the bottom wall to successively narrow the extent of the cavity in a direction away from the aperture. The body may have a shape substantially similar to bodies of housings for dual-modality scanning apparatuses known in the art.

The body (7) of the housing (5) defines a cavity in which selected components of the dual-modality scanning apparatus are housed and an opening (31) which is in communication with the cavity. As best shown for example in FIG. 4, the opening (31) is of rectangular shape with rounded or radiused corners, although it should be appreciated that in other embodiments, the opening may take on other shapes, such as square, circular, oval or the like.

Figure 9:
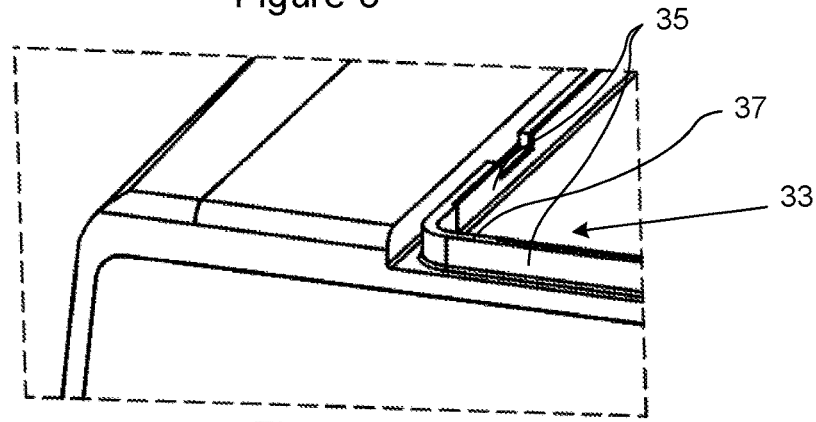
FIG. 9 is an enlarged view illustrating part of a lip formation which surrounds an opening defined in the body of the housing of FIG. 2.
Figure 10:
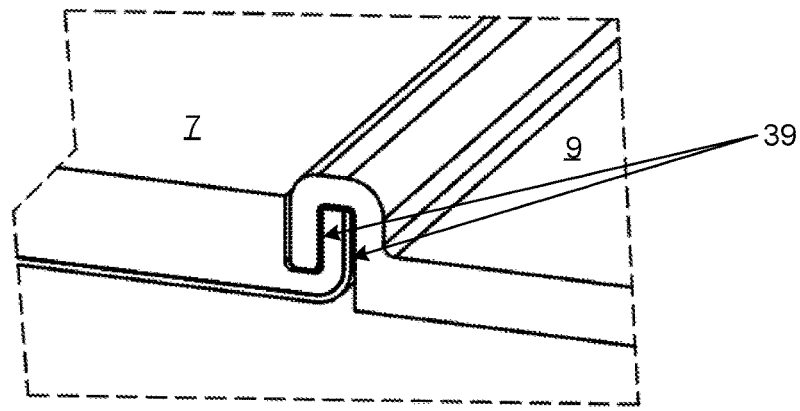
FIG. 10 is an enlarged three-dimensional section view through the line X-X illustrating cooperation of the lip formation and a groove formation formed in the scanning plate of FIG. 3.
Figure 11:
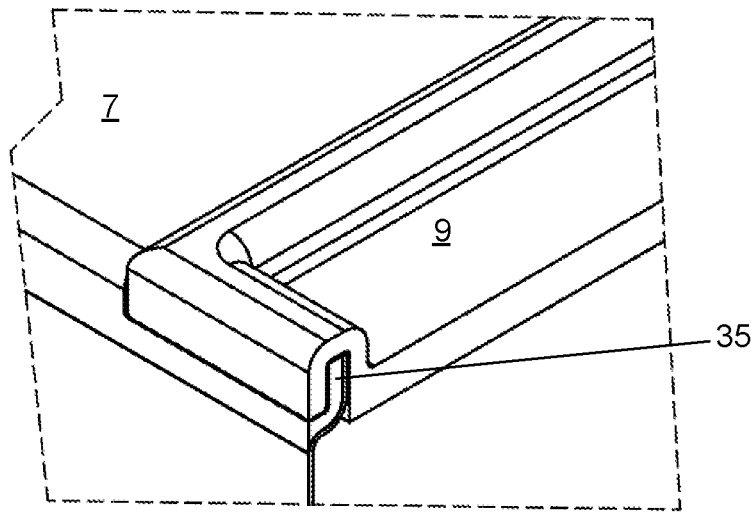
FIG. 11 is an enlarged three-dimensional section view through the line XI-XI illustrating cooperation of the lip and groove formations from another perspective.
Figure 12:
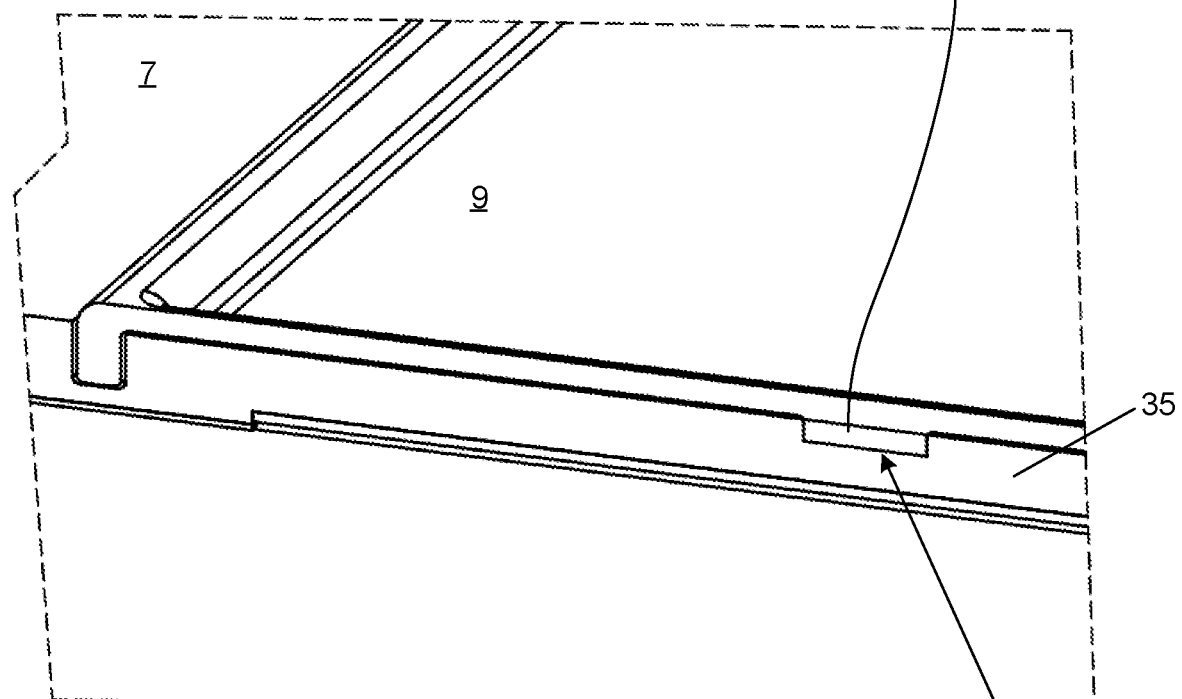
FIG. 12 is an enlarged three-dimensional section view through the line XII-XII illustrating cooperation of the lip and groove formations and castellations thereof.

As shown most clearly for example in FIG. 9, the body (7) includes a lip formation (33) extending from a peripheral zone or area adjacent the opening (31) in a direction away from the cavity and transverse (e.g. 90 degrees) to a plane defined by the opening (31). The peripheral zone or area may be a zone or area of an operatively upper surface of the body (7) which surrounds the periphery defining the opening (31).

The lip formation may be in the form of a wall and may have a height and a width. In the illustrated embodiment the lip formation includes lip elements (35) and corner pieces (37) which are arranged such that the lip formation (33) surrounds the opening (31). The lip elements (35) extend along each side of the opening (31) and are joined to each other at ends thereof by the corner pieces (37). In the illustrated embodiment, the lip formation (33) is thus in the form of a perimeter wall which surrounds the opening (31). In other embodiments, the lip formation may be made up of unjointed or separated lip elements.

In the illustrated embodiment, the lip formation (33) has a width of about 2 mm and a height of about 4.5 mm. The width to height ratio of the lip formation (33) of the illustrated embodiment is 1:2.25, although it should be appreciated that this ratio may be in the range of 1:1.00 to 1:4.00. The width to height ratio may be selected so as to maximize shear loading (particularly so-called "Mode II—In-plane shear" loading) of an adhesive used to bond the scanning plate (9) to the body (7). Shear loading is loading by virtue of a force applied in a direction parallel with a plane of a gap (39), shown for example in FIG. 10, between major surfaces of the lip formation (33) and a groove formation (55) of the scanning plate (9) (described in greater detail below). Mode II—In-plane shear loading is a sliding or in-plane shear mode where the gap surfaces slide over one another in a direction perpendicular to a leading edge of the gap (39). As will be explained in greater detail below, adhesives which exhibit high resistance to Mode II—In-plane shear loading failure may be selected to bond the scanning plate to the body.

The body may be made from a fiber-reinforced polymer, being a composite material made of a polymer matrix and reinforced with fibers. In the illustrated embodiment, the body is made from a carbon fiber-reinforced polymer. In some embodiments, as illustrated for example in FIG. 14, fibers (51) of the carbon fiber-reinforced polymer which form the lip elements (35) may extend in a direction which is generally parallel to the direction in which the lip elements (35) extend. The fibers (51) of the lip elements (35) may thus extend transverse to the plane defined by the opening (31) and parallel to an axis (53) extending from the plane defined by the opening (31). As mentioned in the foregoing, this may in operation align the fibers (51) with the direction of forces typically exerted on the scanning plate (9) (and in turn the adhesive (52)) during operation. Such forces typically arise from the paddle (3) compressing the biological tissue (11) onto the scanning plate (9), although other forces may be present, for example forces caused by the sealed and filled nature of the housing (5) and/or due to any expansion of fluid therein.

The scanning plate may be made from PMP. The scanning plate (9) is shaped and dimensioned to close the opening (31) and may have a groove formation (55) extending along a periphery thereof and being shaped and dimensioned to cooperate with and receive the lip formation (33). The groove formation (55) may be provided by a channel or furrow which is machined into an operatively underside of the scanning plate (9). The groove formation (55) may have a depth and width which corresponds to the height and width of the lip formation (33) such that the lip formation (33) may be received within the groove formation (55). In some implementations, the groove formation is machined into an enlargement which surrounds the scanning plate and which defines, on an operatively upper side of the scanning plate, a recessed scanning surface.

The scanning plate (9) has a shape which corresponds to that of the opening of the body, in the illustrated embodiment, being rectangular in shape. The groove formation (55) may be considered to include groove elements extending along each side of the scanning plate (9) and which are joined at their ends by corner pieces to provide an endless groove surrounding the scanning plate (9). The groove formation may however be a continuous groove which circumnavigates the scanning plate. The groove may be arranged so as to cooperate with the lip formation of the body of the housing.

In the illustrated embodiment, the groove and lip formations (55, 33) include cooperating castellations at locations along the lengths thereof. The lip formation (33) (or lip elements (35) thereof) for example may include recesses (57) formed or defined at selected points therein. The groove formation (55) may include raised portions (59) which are shaped and dimensioned to fit within the recesses (57) and which are at locations along the groove formation (55) selected so as to cooperate with the raised portions (59). The castellations may improve tolerance to longitudinal stress that can arise from the different rates of thermal expansion of the body and the scanning plate (or, e.g., of the carbon-fiber reinforced polymer and the PMP). Such longitudinal stresses may be transferred as compression stresses in the body of the housing and the scanning plate which may in turn reduce the longitudinal shear stress that would be carried by the adhesive.

The scanning plate (9) may be fitted to the body (7) with the lip and groove formations (33, 55) (and any castellations formed therein) cooperating with each other. This may entail the lip formation (33) being received by the groove formation (55) such that major surfaces of the lip formation (33) locate face-to-face with major surfaces of the groove formation (55). An adhesive or other bonding agent may be applied to major surfaces of one or both of the lip formation (33) or the groove formation (55) so as to bond the scanning plate (9) to the body (7).

The adhesive may be a structural acrylic adhesive and may be selected for its sufficiently high resistance to Mode II—In-plane shear loading failure. 3M™ Scotch-Weld™ Structural Plastic Adhesive DP8010 is an example of a suitable structural acrylic adhesive although there may be other suitable alternatives. As mentioned in the foregoing, the lip and groove formations (33, 55), in particular the shape and arrangement of the lip and groove formations, maximize bonded surface area, particularly in the shear direction in which the adhesive bond is strongest.

The adhesive may bond the screening plate to the body with sufficient strength to withstand forces expected to be exerted on the bond during normal operation of the housing. The adhesive, cooperating with the lip and groove formations may provide an airtight seal to facilitate hermetic sealing of the housing and filling with non-conductive fluid. Sufficient bond strength may be achieved by virtue of the lip and groove formation (and the width to height ratio thereof), the selected bonding agent and/or due to the specific alignment of fibers in the lip elements of the body.

A method of manufacturing a body of a housing, such as the housing described in the foregoing, is now described with reference to FIGS. 15 to 23. The body may be manufactured using fiber-reinforced polymer. The method may include providing (201) a fiber-reinforced polymer layup. The fiber-reinforced polymer may be pre-impregnated fiber-reinforced polymer. For example, thermoset polymer material or the like may already be present and used to bond fibers together. The thermoset polymer material may be only partially cured to allow for handling and manipulation onto a shell or mold piece. The polymer of the fiber-reinforced polymer may be of the epoxy type (e.g. an epoxy resin). The fiber-reinforced polymer layup may be provided in sheets or matts of fiber-reinforced polymer. Fibers in the sheets may be in the form of a weave. Fibers in the sheets may thus run in two directions, with fibers running in the first direction being perpendicular to fibers running in the second direction. Reference herein to the "direction of fibers", or the like, is a reference to one of the two possible directions of the fibers in a given sheet of fiber-reinforced polymer (or a portion of the housing which is formed from such sheet or sheets). In some implementations, the fiber-reinforced polymer may be carbon fiber-reinforced polymer and the sheets, or matts, of fiber-reinforced polymer may be sheets or matts of carbon-fiber weave pre-impregnated with polymer epoxy.

Figure 16A:
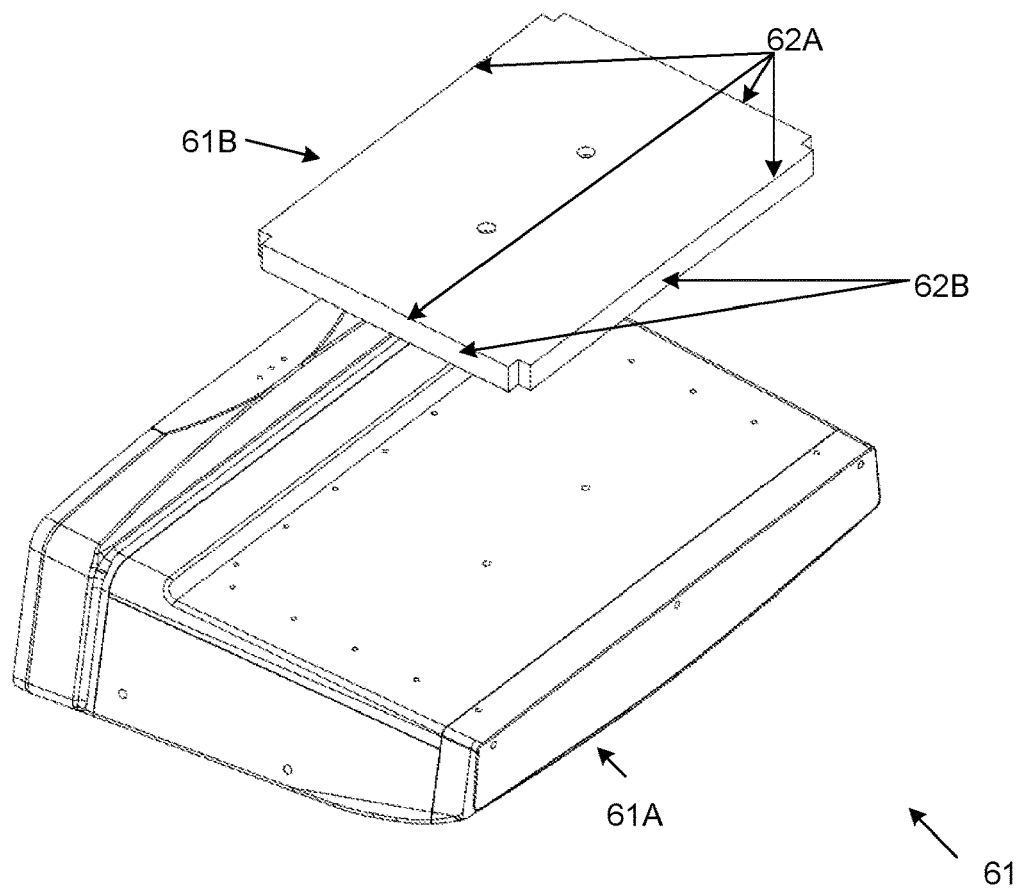
FIG. 16A is a three-dimensional view illustrating parts of a tooling mold onto which the body of the housing is molded, with the parts being separated.
Figure 16B:
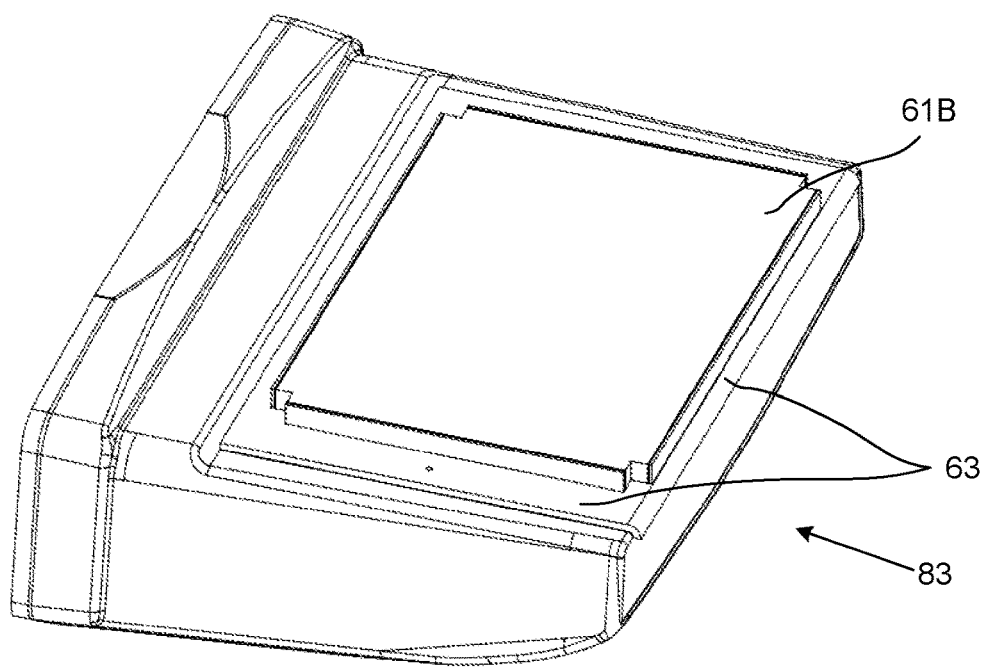
FIG. 16B is a three-dimensional view illustrating the pre-machined body molded onto the tooling mold and including excess material.

The method may include molding (203) the fiber-reinforced polymer layup into the shape of the body. For example, and as shown in FIGS. 16A and 16B, the layup may be molded onto a shell or mold piece (61) so as to define the walls of the mold and the cavity in which components are to be housed. The shell (61) may be made from aluminum and may define the shape of the body which is to be molded. The shell (61) may be a male mold made of two parts (61A, 61B), which can be detachably secured to each other (e.g. by way of bolts or other suitable fasteners). Fiber-reinforced polymer may be molded over both parts (when secured to each other). When removing the shell (61), the parts may be separated from each other to allow the major part (61A) to be removed from the cavity through an aperture to be closed by a backplate.

The method may include controlling (205) the fiber direction of the fiber-reinforced polymer so that at least some of the fibers which form the lip formation are arranged to extend generally parallel to the direction in which the lip formation extends. This may include arranging the layup on the shell in a way that maximizes those portions of the layup that will form lip elements of the lip formation having a fiber direction that is transverse to the direction in which the relevant lip element runs. For example, a number of individual sheets of fiber-reinforced polymer may be used. Each of the sheets may be marked with an indication of the direction in which fibers thereof run. The individual sheets may then be arranged to define the walls of the body. The sheets may be arranged on the shell such that edges thereof which run transverse to the fiber direction thereof originate or terminate on or proximate upper edges (62) of the minor part (61B) of the shell and extend therefrom along minor surfaces (62B) of the minor part towards a corner defined by the join of the minor part and the major part of the shell. From here, the sheets bend with the corner and extend along and around the major part of the shell in such a way as to define the body. The sheets may be cut such that they meet and can be joined together to form edges of the body. In this way, the lip formation that will ultimately be formed from these sheets of material (and specifically from those portions of the sheets that run along the minor surfaces of the minor part of the shell) will have a fiber direction that extends with or along the height of the lip formation (as opposed to, e.g., through or along a thickness or width of the lip formation). Sheets of fiber-reinforced polymer may thus be arranged on the shell such that those edge portions of the layup that will ultimately form lip elements of the lip formations have a fiber direction that is transverse to the edge of the edge portion of the sheet of fiber-reinforced polymer.

Figures 17, 18, 19, 20A, 20B:
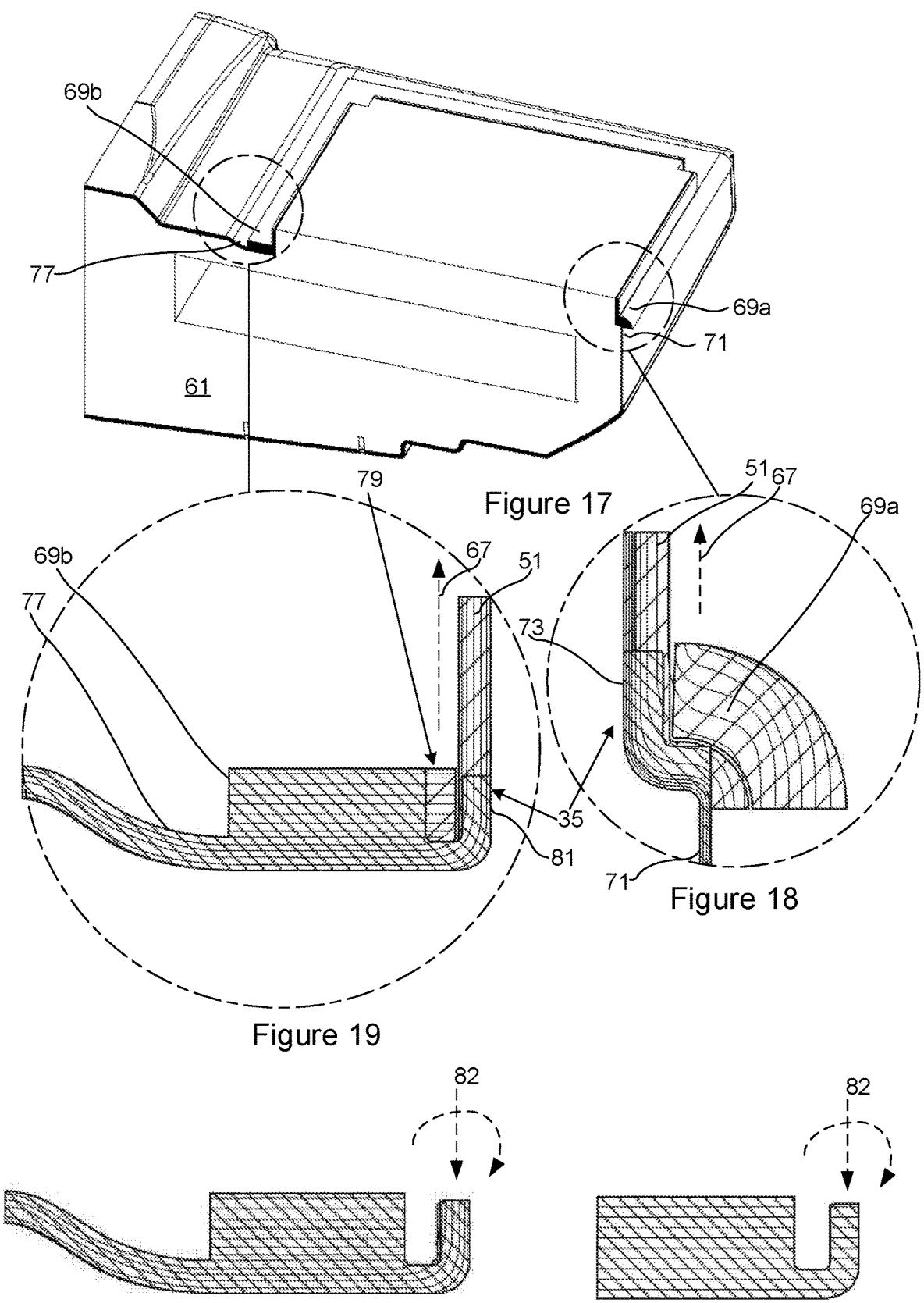
FIG. 17 is a three-dimensional sectional view of the pre-machined, molded body of FIG. 16B.
FIG. 18 shows, in enlarged schematic form, a first encircled region of FIG. 17 so as to illustrate the orientation of fibers of the fiber-reinforced polymer from which the pre-machined, molded body is formed, cross-hatching is used to differentiate between material that is removed in the machining process and material that remains thereafter.
FIG. 19 shows, in enlarged schematic form, a second encircled region of FIG. 17 so as to illustrate the orientation of fibers of the fiber-reinforced polymer from which the pre-machined, molded body is formed, cross-hatching is used to differentiate between material that is removed in the machining process and material that remains thereafter.
FIG. 20A is a schematic diagram which illustrates the effect of forces on elements formed with a preferred fiber orientation.
FIG. 20B is a schematic diagram which illustrates the effect of forces on elements formed with another fiber orientation.

For example, with reference to FIGS. 18 and 19, the direction of the fibers (51) of that part of the layup that will constitute the lip elements (35) may be controlled so as to extend generally parallel to each other and upwards (67) or in the direction of the height of the wall forming the lip elements (35). In other words, the fibers (51) may run parallel to the lip element (35), as opposed to across it.

Providing fibers (51) extending in such a direction may require the use of excess material (63) in the layup which is manipulated so as to control the fiber direction as required. The method may include adding (206) excess material to the layup as separate portions of carbon fiber-reinforced polymer material. The excess material may be added to reinforce portions of the layup. The layup may thus be molded with excess material (63). The excess material (63) may be added to the layup as separate portions of carbon fiber-reinforced polymer material (69) which, after curing, become integrally formed to provide a unibody. Some portions of excess material may be added with fibers thereof extending parallel to fibers already constituting the layup and may be arranged specifically to facilitate appropriate fiber direction of the lip elements.

For example, with reference again to FIG. 18, portions of excess material (69a) are added to a fiber-reinforced polymer sheet which will form the side wall of the body being opposite the aperture. The portions of excess material are added with a fiber direction extending parallel to fibers of the layup forming a side wall (71) of the body. The excess material (69a) may be provided to increase thickness of a lip wall (73) which extends from the side wall (71) and which provides the lip elements (35) of the lip formation (33) after machining. Fibers of the excess material (69a) are arranged so as to run with (as opposed to, e.g., across) fibers of the carbon fiber-reinforced polymer layup which provides the side wall of the body.

Similarly, with reference to FIG. 19, portions of excess material (69b) are added to a fiber-reinforced polymer sheet which will form the top wall of the body. The portions of excess material are added with a fiber direction extending with (in this case generally parallel to) fibers of the layup forming a top wall (77) of the body. The excess material (69b) may be however limited in its length, or may be machined, so as to provide a space (79) between an end portion thereof and a lip wall (81) which is formed by bending the layup forming the top wall (77) of the body transversely away from what will become the cavity.

Fiber direction may thus be carefully controlled so as to align fibers (51) in a direction that provides maximum strength to the adhesive joint geometry.

Arranging the fiber direction of lip elements as such may increase strength of the adhesive joint geometry. For example, as illustrated in FIG. 20A, correct fiber alignment loads fibers of the carbon fiber-reinforced polymer whereas incorrect alignment, as illustrated in FIG. 20B, loads polymer bonding the fibers. In other words, having the fibers running along the direction of the lip (as illustrated in FIG. 20A) means that the fibers carry the load (82) (this load results when the scanning plate is compressed downward) whereas having fibers running across the direction of the lip (as illustrated in FIG. 20B) causes resin to carry the load (82).

Figure 21A:
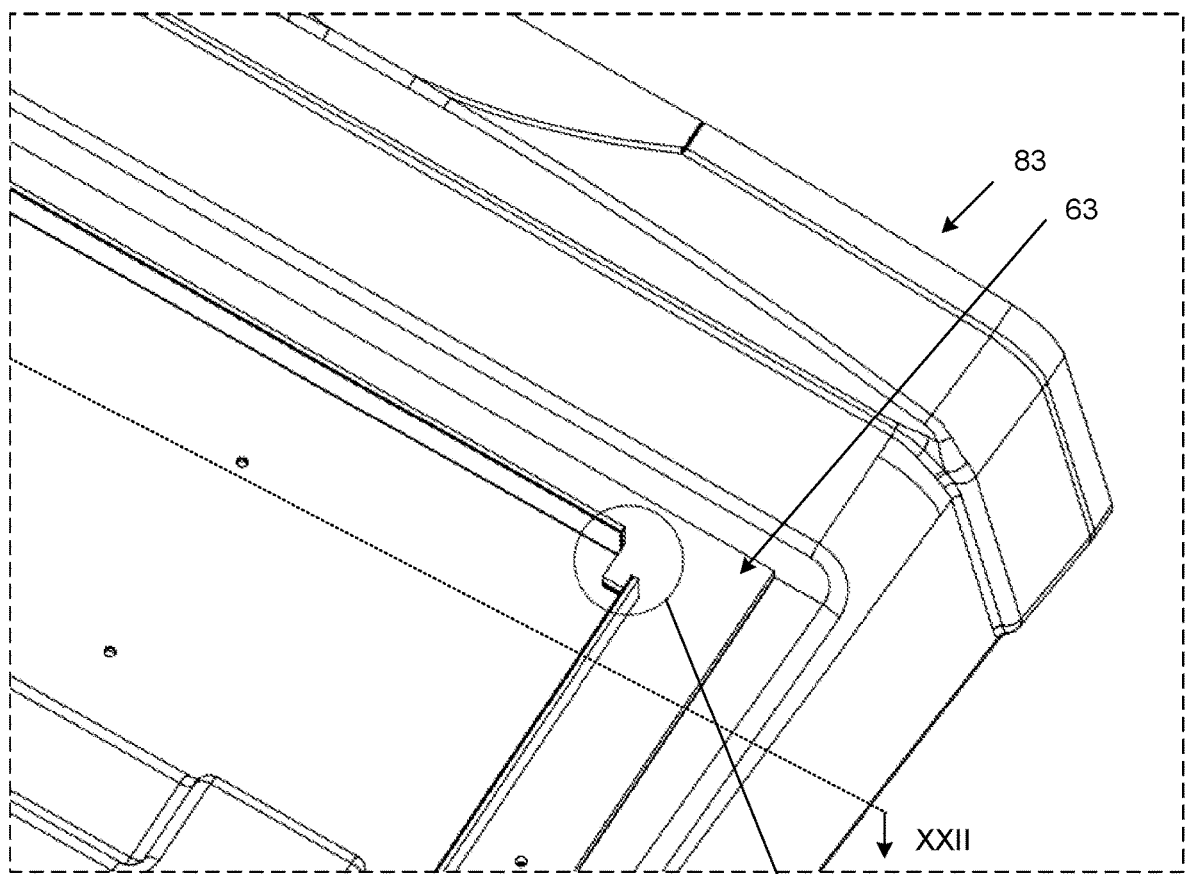
FIG. 21A is another three-dimensional view of a part of the pre-machined, molded body of FIG. 16B which illustrates corner pieces of the lip formation.
Figure 21B:
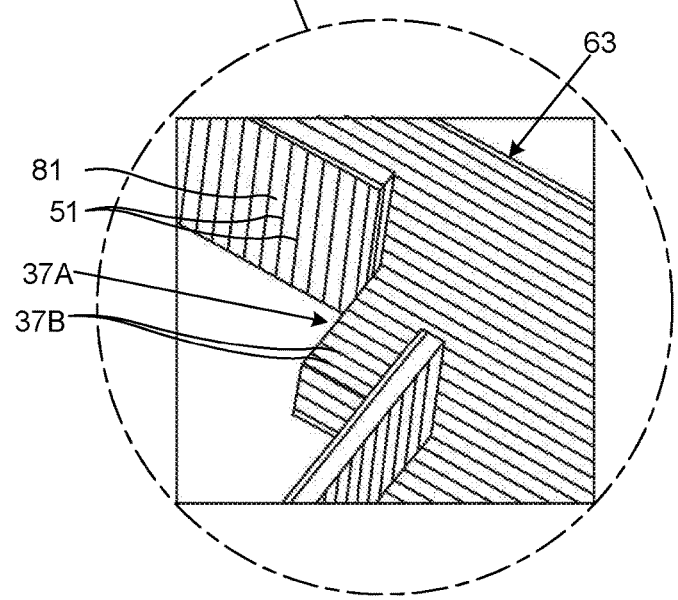
FIG. 21B shows, in enlarged schematic form and from another perspective, an encircled region of FIG. 21A so as to illustrate the orientation of fibers of the fiber-reinforced polymer from which the pre-machined, molded body is formed.
Figures 22A, 22B:
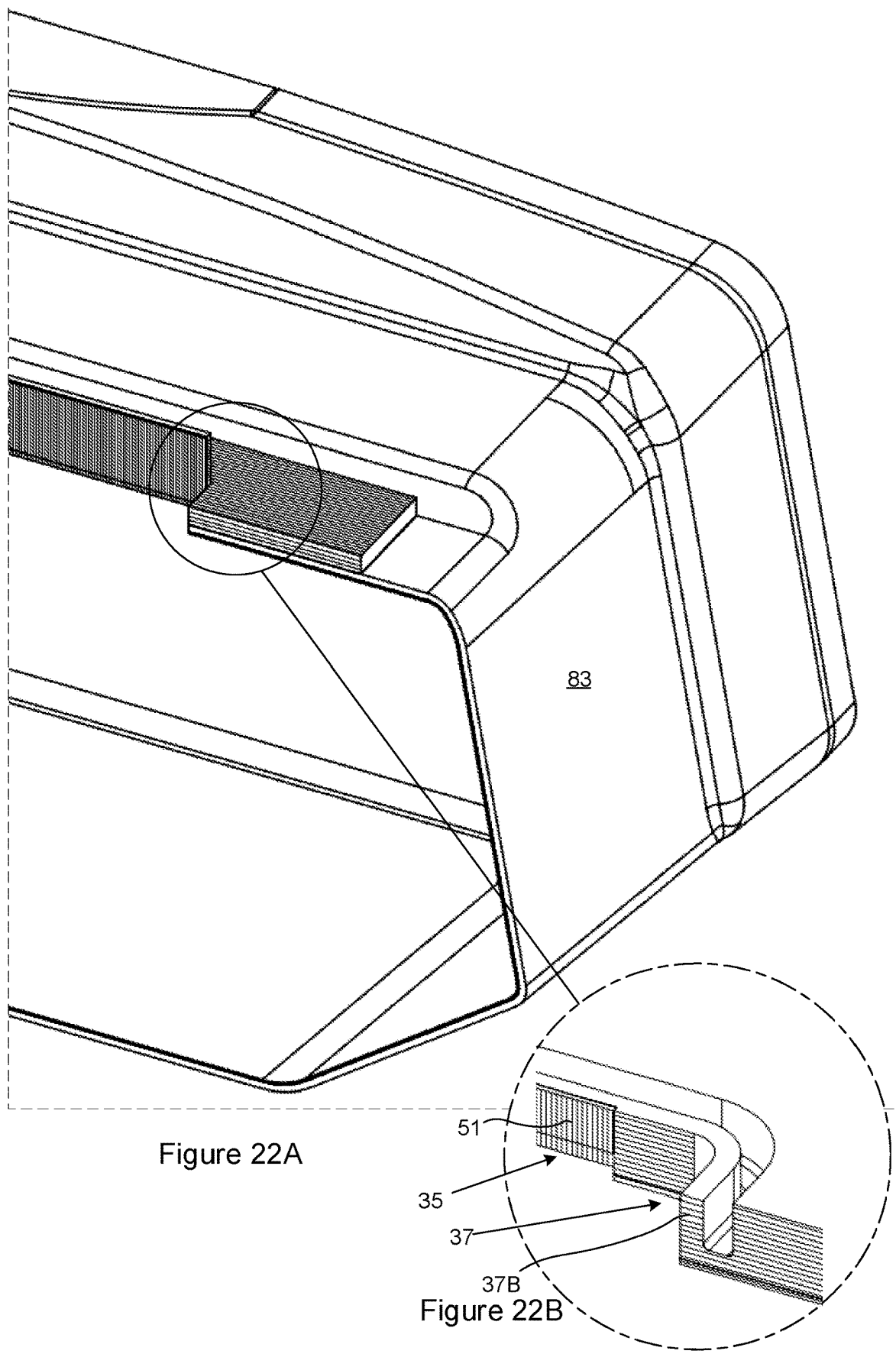
FIG. 22A is a three-dimensional sectional view through the line XXII-XXII of a part of the pre-machined, molded body of FIG. 16B which illustrates fiber orientation of fibers forming part of a lip element and excess material.
FIG. 22B illustrates the encircled region of FIG. 22A after machining of the excess material to define a corner piece of the lip formation.
Figure 23:
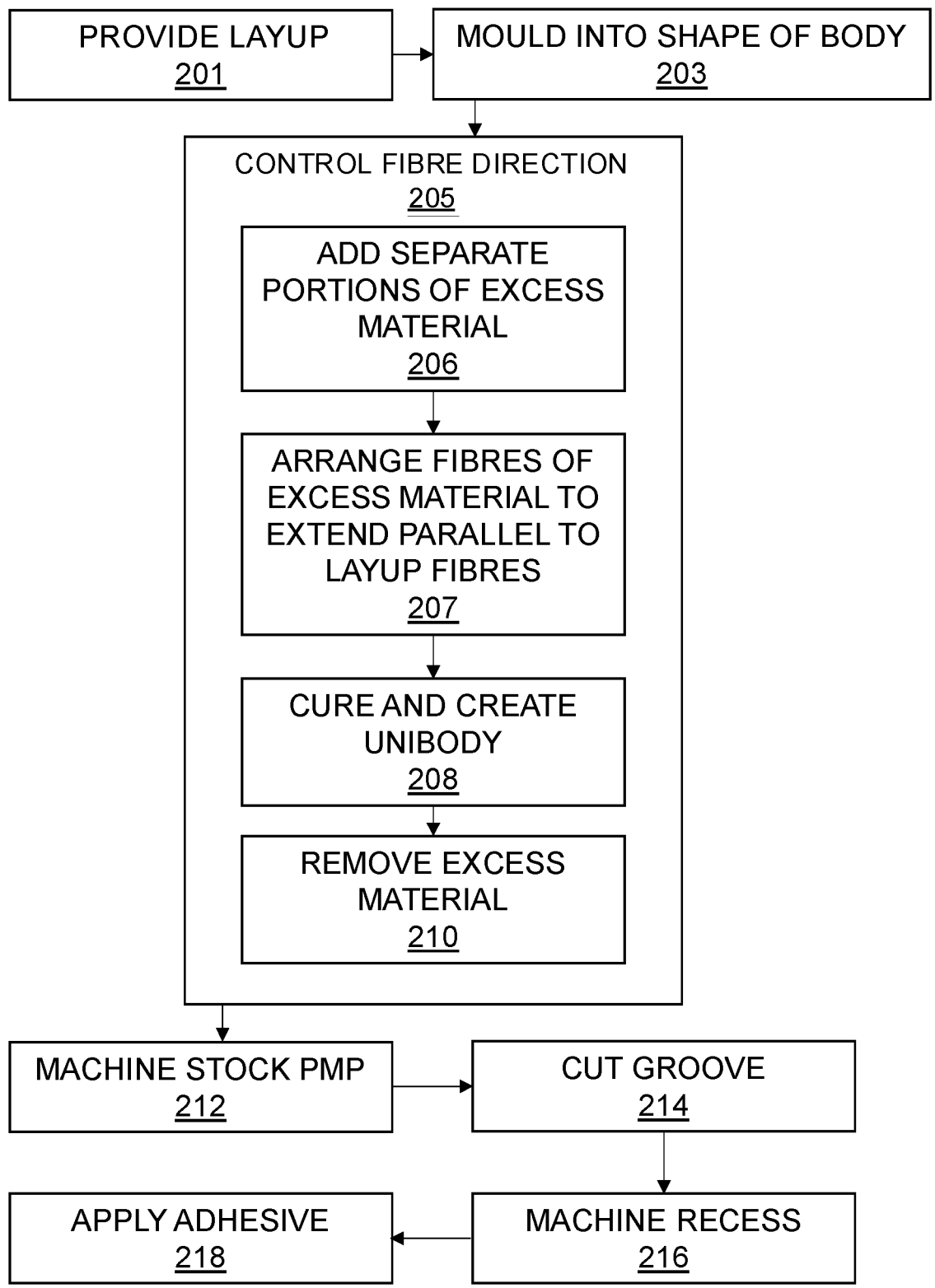
FIG. 23 is a flow diagram of an example embodiment of a method of manufacturing a body of an imaging system housing in accordance with aspects of the present disclosure.

Corner pieces of the lip formation may be formed from excess material, as shown most clearly in FIGS. 21 to 22. The excess material added to sheets of fiber-reinforced polymer on the shell that form the top wall of the housing may be arranged to abut or almost abut those portions of the sheets that form the lip elements. This excess material may be added so as to fill corner cut-outs of the minor piece (61B) of the shell (61). Filling these cut-outs forms protruded portions (37A) of material that extend into what will become the opening after machining. The direction of fibers (37B) of these protruded portions is parallel to fiber direction of the top wall, and transverse to the direction of fibers (51) in the sheets of material that form the lip elements. During the machining process, these protruded portions may be machined away which, together with a channel machined in the excess material, define the corner piece (37), as illustrated in FIG. 22B.

Thus, in some implementations, for example as illustrated in FIGS. 21 to 22, corner pieces (37) of the lip formation may have a fiber direction which is transverse to the direction of the fibers in the lip elements (35). The fibers of such corner pieces may run across the corner pieces and not parallel to a height through which the corner pieces extend. This compromise may be accepted so as to prevent the fiber-reinforced polymer sheets from bunching. Bunching may occur if the carbon fiber-reinforced sheet was forced to bend at the corner to try and align the fibers in the correct direction. A bend in the carbon fiber-reinforced sheet will create an uneven, bulged surface and negatively affect the working of the housing. Therefore, excess material (63) is used to create well-defined corners as clearly illustrated in FIG. 21B but at the cost of not having the fibers in the optimal condition at these sections. The excess material (63) allows for the corner pieces to be shaped, e.g. by machining, after the mold has cured to produce well-defined corner pieces.

The layup may be cured (208) using an autoclave to provide a pre-machined, molded body (83). Once cured, the pre-machined, molded body (83) is mounted in a jig to allow machining where the excess material (63) is removed to provide the body (7). Excess material may be removed (210) using known machining techniques.

Stock PMP forming the scanning plate may be machined (212) to a thickness of between 2 and 6 mm and may be cut to size to provide a substantially rectangular plate (optionally with rounded corners) having a periphery which conforms to that of and closes the opening of the body.

The PMP may be cut (214) to define the groove formation which extends along the periphery of the scanning plate. The depth and width of the cut may be selected so as to cooperate with the height and width of the lip formation of the body. In some implementations, a recess is machined (216) into an operatively upper surface of the PMP to provide an enlargement which surrounds the scanning plate (and into which the groove formation is defined) and a recessed scanning surface. The recessed scanning surface may be formed so as to reduce the thickness of the PMP between transducer and tissue.

An adhesive may be applied (218) to major surfaces of one or both of the lip formation (33) or the groove formation (55). The scanning plate (9) may be brought towards the body (7) with the groove formation (55) aligned with the lip formation (33) until the lip formation (33) receives the groove formation (55). The adhesive contacts and adheres to surfaces of the lip and groove formation (33, 55) so as to bond the scanning plate (9) to the body (7).

With the scanning plate secured to the body, assembly of the imaging device may continue, for example including fitting required components within the cavity, fitting a backplate to the body of the housing and sealing and filling the housing with a suitable non-conductive fluid.

Figure 24:
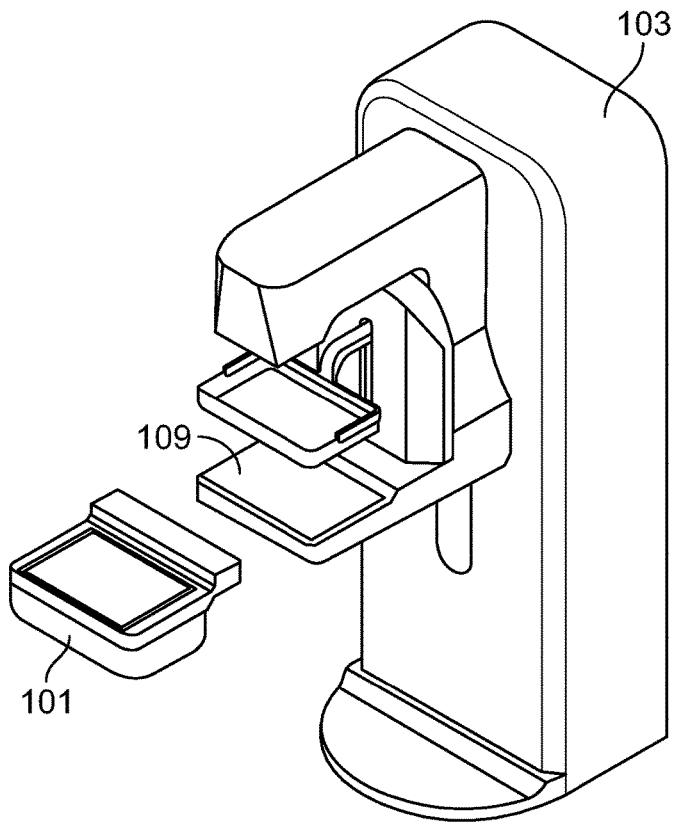
FIG. 24 is a three-dimensional view of an imaging device which is configured for attachment to a mammography device so as to provide an after-market dual-modality scanning apparatus according to aspects of the present disclosure, in which the imaging device is spaced apart from an imaging panel of the mammography device.
Figure 25:
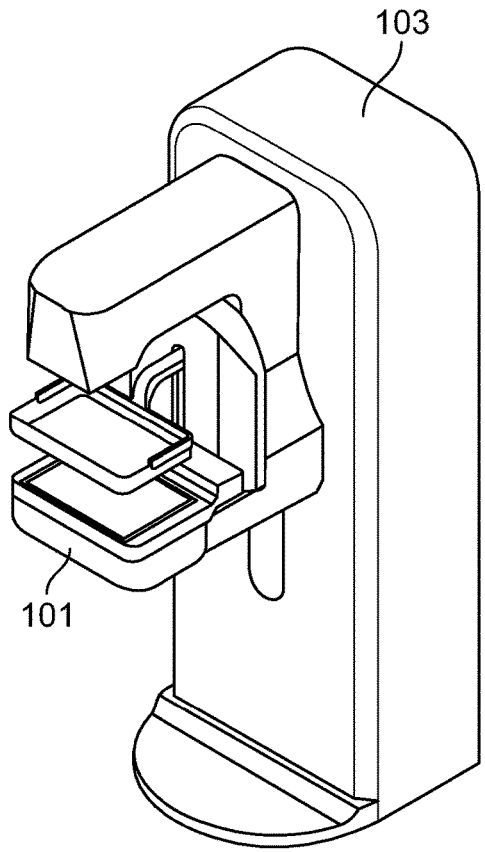
FIG. 25 is similar to FIG. 24, except in that the imaging device is attached to the imaging panel of the mammography device; and, FIG. 26 is an enlarged three-dimensional view of the imaging device attached to the imaging panel of the mammography device.
Figure 26:
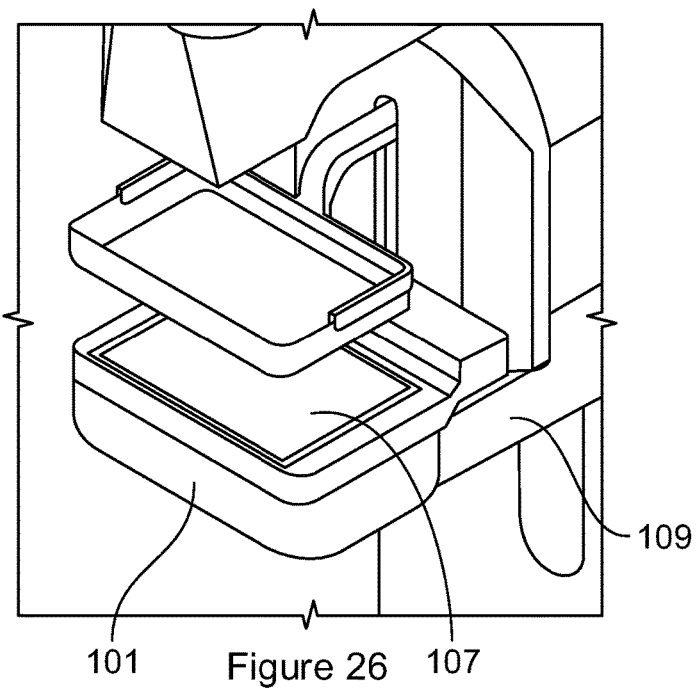

As mentioned in the foregoing, embodiments of the present disclosure provide a housing for an imaging device which is configured for attachment to a mammography (or similar) device so as to provide an after-market dual-modality scanning apparatus. FIGS. 24 to 26 illustrate an exemplary housing (101) for an imaging device which is configured to be attached or otherwise secured to a mammography device (103) of the type that acquires X-ray images using a flat panel detector (also referred to as an imaging panel). The housing may be similar to that described above with reference to FIGS. 1 to 23 and any features or characteristics of the previously described housing may be present in the embodiment of the housing illustrated in FIGS. 24 to 26.

The housing (101) of FIGS. 24 to 26 may differ primarily in that a smaller cavity may be provided for housing a scanning element including an ultrasonic transducer. The ultrasonic transducer may be mounted on rails below a scanning plate (107) of the housing (101). The ultrasonic transducer moves on the rails in a plane parallel to the scanning plate for imaging of tissue through the scanning plate and parallel to a plane defined by the transverse movement of the X-ray source provided by the mammography device (103).

The rails may be provided at locations which are outside of the field of view of the X-ray source. The cavity may include a zone which locates outside of the field of view of the X-ray source for receiving the ultrasonic transducer during operation of the X-ray source. A linear drive means, also outside the field of view of the X-ray source, is provided that moves the ultrasonic transducer along the rails. The housing may be hermetically sealed and filled with fluid as described in the foregoing.

The housing (101) may include a formation which is configured to receive a flat panel detector (109) of the mammography device (103). The formation may define a recess which is shaped and dimensioned to receive the panel detector. The formation may be defined at a location relative to a cavity of the body of the housing (101) such that the scanning plate of the housing (101) is parallel to and directly above an operatively upper surface of the flat panel detector. This may locate the ultrasonic transducer between the flat panel detector and the scanning plate (107). The ultrasonic transducer may be configured to scan across the underside of the scanning plate after the X-ray full field exposure and the associated X-ray grid has been retracted to obtain the ultrasound volume imaging data of the relevant biological material.

Embodiments of the present application provide a housing for an imaging device which is hermetically sealed and filled with a non-conductive fluid with an acoustic impedance resembling that of biological tissue. The housing may house components of the imaging device which are operatively immersed in the non-conductive fluid. A cooperating lip-and-groove formation is provided in the body and scanning plate of the housing to facilitate bonding the scanning plate to the body using a suitable structural acrylic adhesive in a sealed fashion so as to provide the required hermetic sealing. The scanning plate may be made from a material with low LSE (such as polymethylpentene) and the lip and groove formation may be configured so as to maximize adhesive bonding in the 'shear direction' so as to improve the strength of the bond. Further, the body of the housing may be made from a fiber-reinforced polymer. Orientation of fibers located in the lip/groove formation provided by the body may be arranged so as to extend parallel to an axis of, and transverse to an operatively upper surface of, the scanning plate. The housing may be used in a dual-modality scanning apparatus or to retrofit single-modality mammography devices with ultrasound scanning capabilities.

It should be appreciated that the scanning plate must preferably be manufactured from a material which will be able to withstand the compression forces exerted on it by the compressed biological tissue being imaged. These forces may be as high as 200 N acting over a minimum surface area of 100×100 mm. It has been found that PMP exhibits adequate material strength properties to warrant its use in the scanning assembly. PMP is a high-performance polyolefin resin with a low density, low dielectric properties, high transparency and low refractive index. Most importantly, it has a lower acoustic impedance (1.84 MRayl) than most other plastic materials with suitable mechanical strength. PMP provides an acoustic match to both the ultrasonic transducer and the biological tissue (notably breast tissue), which makes it an ideal material for use as a scanning surface on a platform for dual-modality mammography. However, PMP also has a very low surface tension (which is a result of its low surface energy), providing it with exceptional peel ability. This physical property of PMP poses a problem associated with fixing a PMP scanning plate into or onto the body to obtain a hermetic seal. It has been found that the housing and method of manufacture described in the foregoing overcome these difficulties in that a hermetic seal between the body and the scanning plate is provided which performs sufficiently for dual-modality scanning apparatuses.

As described, the hermetically sealed housing may be filled with a non-conductive fluid with a specific acoustic impedance that resembles the acoustic impedance of the biological tissue to be scanned. In the case of it being breast tissue, an acoustic impedance of about 1.3 MRayl is appropriate. Mineral oil achieves adequate acoustic coupling between the ultrasound transducer, the scanning plate and the breast tissue. The filling of the housing with oil (which oil may be mineral oil and which may be de-gassed prior to filling) is conducted during a filling and bleeding process which removes substantially all air from the housing.

The above description is by way of example only and it should be appreciated that numerous changes and modifications may be made to the methods and products described without departing from the scope of the invention as set out in the claims. For example, it may be that a groove formation is defined in the body and a lip formation defined in the scanning plate. It will be appreciated by a person skilled in the art that the shape and size of the opening in the body for the scanning plate and the scanning plate itself may vary according to requirements. Further, it may be that the width to height ratio of the lip (and hence the width to depth ratio of the groove) is in the range of 1:1 to 1:5, 1:1.5 to 1:4, 1:1.7 to 1:3.8, 1:1.78 to 1:4, 1:2.0 to 1:2.5, 1:2.10 to 1:2.40, 1:2.20 to 1:2.30, or the like.

Although the above description is directed towards the bonding of polymethylpentene to a fiber-reinforced polymer, such as a carbon fiber-reinforced polymer, aspects of the present disclosure may find applications in bonding other low surface energy plastics materials, such as polypropylene ("PP"), polyethylene ("PE"), high density PE ("HDPE"), polystyrene, acetal, EVA (ethylene vinyl acetate), powder-coated paints and the like to various types of composite.

Throughout the specification and claims unless the contents requires otherwise the word 'comprise' or variations such as 'comprises' or 'comprising' will be understood to imply the inclusion of a stated integer or group of integers but not the exclusion of any other integer or group of integers.

The invention claimed is:

1. An imaging system housing comprising a body and a scanning plate, the body defining a cavity and an opening in communication with the cavity, the body including a lip formation extending from a peripheral zone adjacent the opening in a direction away from the cavity and transverse to a plane defined by the opening, the scanning plate being shaped and dimensioned to close the opening and having a groove formation extending along a periphery thereof and being shaped and dimensioned to cooperate with and receive the lip formation of the body, wherein the scanning plate is made from a low surface energy (LSE) plastic material, and wherein the body and plate are bonded together using a structural acrylic adhesive applied to one or both of the lip and groove formations, wherein the body is made from a fiber-reinforced polymer, and wherein fibers of at least portions of the fiber-reinforced polymer which form at least part of the lip formation extend transverse to the plane defined by the opening.

2. The housing of claim 1, wherein the scanning plate is made from polymethylpentene.

3. The housing of claim 1, wherein the groove and lip formations include cooperating castellations at locations along lengths of the groove and lip formations respectively.

4. The housing of claim 1, wherein the width to height ratio of the lip formation is in the range of 1:1.00 to 1:4.00.

5. The housing of claim 1, wherein the housing includes a formation configured to receive a flat panel detector of an imaging device, wherein the formation defines a recess which is shaped and dimensioned to receive the flat panel detector, and wherein the formation is defined at a location relative to the cavity of the body so as to orient operatively the scanning plate parallel to and directly above an operatively upper surface of the flat panel detector.

6. The housing of claim 1, wherein the opening and scanning plate are rectangular in shape.

7. The housing of claim 6, wherein the lip formation includes lip elements extending along each side of the opening and corner pieces which join the lip elements to define a lip which surrounds the opening.

8. The housing of claim 7, wherein fibers of the fiber-reinforced polymer which form the lip elements extend transverse to the plane defined by the opening.

9. The housing of claim 1, wherein the lip formation includes lip elements and corner pieces which are arranged such that the lip formation surrounds the opening.

10. The housing of claim 1, wherein the fiber-reinforced polymer is a carbon fiber-reinforced polymer.

11. The housing of claim 1, wherein the housing is hermetically sealed, wherein components of an imaging system are located within the cavity and wherein the housing is filled with a non-conductive fluid having a specific acoustic impedance.

12. The housing of claim 11, wherein the housing is configured to house an X-ray detector and ultrasonic transducer below the scanning plate.

13. The housing of claim 1, wherein the groove formation defines a groove which surrounds the scanning plate.

14. The housing of claim 9, wherein fibers of the fiber-reinforced polymer which form the lip elements extend transverse to the plane defined by the opening.

* * * * *